United States Patent
White et al.

(10) Patent No.: US 11,174,478 B2
(45) Date of Patent: Nov. 16, 2021

(54) SINGLE-STEP DNA PREPARATION FOR POLYMERASE CHAIN REACTION USING MAGNETIC CHITOSAN MICROPARTICLES

(71) Applicants: University of Maryland, College Park, MD (US); Canon U.S.A., Inc., Melville, NY (US)

(72) Inventors: Ian M. White, Ellicott City, MD (US); Srinivasa Raghavan, Columbia, MD (US); Kunal R. Pandit, Laurel, MD (US); Imaly Nanayakkara, College Park, MD (US); Weidong Cao, North Potomac, MD (US)

(73) Assignees: University of Maryland, College Park, College Park, MD (US); Canon U.S.A., Inc., Melville, NY (US)

( * ) Notice: Subject to any disclaimer, the term of this patent is extended or adjusted under 35 U.S.C. 154(b) by 524 days.

(21) Appl. No.: 15/160,935

(22) Filed: May 20, 2016

(65) Prior Publication Data

US 2016/0340668 A1 Nov. 24, 2016

Related U.S. Application Data

(60) Provisional application No. 62/323,188, filed on Apr. 15, 2016, provisional application No. 62/164,394, filed on May 20, 2015.

(51) Int. Cl.
| C12Q 1/68 | (2018.01) |
| C12N 15/10 | (2006.01) |
| C12Q 1/686 | (2018.01) |
| B01L 7/00 | (2006.01) |
| B01L 3/00 | (2006.01) |

(52) U.S. Cl.
CPC ......... *C12N 15/1013* (2013.01); *C12Q 1/686* (2013.01); *B01L 3/502753* (2013.01); *B01L 7/52* (2013.01)

(58) Field of Classification Search
None
See application file for complete search history.

(56) References Cited

U.S. PATENT DOCUMENTS

| 6,942,169 B2 * | 9/2005 | Sparks | C12N 1/066 241/1 |
| 10,072,258 B2 | 9/2018 | Faltin et al. | |
| 2007/0015185 A1 | 1/2007 | Basehore et al. | |
| 2008/0181964 A1 | 7/2008 | Kim et al. | |
| 2009/0215124 A1 | 8/2009 | Cao et al. | |
| 2010/0129878 A1 | 5/2010 | Parthasarathy et al. | |
| 2012/0058195 A1 | 3/2012 | Harel | |
| 2015/0184218 A1 * | 7/2015 | White | C12Q 1/24 435/30 |

FOREIGN PATENT DOCUMENTS

| JP | H5-331203 A | 12/1993 |
| WO | 2008/134472 A1 | 11/2008 |
| WO | 2015/018707 A1 | 2/2015 |

OTHER PUBLICATIONS

Horak et al. (J Sep Sci, 2007, 30, 1751-1772) (Year: 2007).*
Tallury et al. (Chem Commun, 2009, 2347-2349) (Year: 2009).*
Heermann et al. (J of Virol Methods, 1994, 50:43-58) (Year: 1994).*
Jiang et al. (Analytical Biochemistry 2012, 420:20-25) (Year: 2012).*
Wang et al., "Electrostatic droplets assisted in situ synthesis of superparamagnetic chitosan microparticles for magnetic-responsive controlled drug release and copper ion removal," J. Mater. Chem. B., vol. 1, pp. 2205-2212 (2013).
Jiang, Cheng, et al., "Chitosan functionalized magnetic particle-assisted detection of genetically modified soybeans based on polymerase chain reaction and capillary electrophoresis," Analytical Biochemistry, vol. 420, No. 1, pp. 20-25 (2012).
Marty, Florence, et al., "Evaluation and optimization of nucleic acid extraction methods for the molecular analysis of bacterial communities associated with corroded carbon steel," Biofouling, vol. 28, No. 4, pp. 363-380 (Apr. 2012).
Jinru Chen et al., "Detection of Verotoxigenic *Escherichia coli* by Magnetic Capture-Hybridization PCR," Applied and Environmental Microbiology, vol. 64, No. 1, pp. 147-152, Jan. 1998. (Exhibit 1).
Jinru Chen et al., "Magnetic Capture Hybridization Polymerase Chain Reaction," Food Microbiology Protocols, Methods in Biotechnology, vol. 14, (2001), pp. 107-110 (9 total pages). (Exhibit 2).

* cited by examiner

*Primary Examiner* — Stephanie K Mummert
(74) *Attorney, Agent, or Firm* — Rothwell, Figg, Ernst & Manbeck, P.C.

(57) ABSTRACT

The present invention relates to a method for concentrating a biological sample containing nucleic acids by using magnetic chitosan microparticles and subsequently performing a PCR reaction on the nucleic acids captured on the microparticles. The chitosan microparticles added to the biological sample at a PCR compatible pH are mechanically agitated to provide for cell lysis and simultaneous DNA capture, and then serve as a solid support for the nucleic acid template during the PCR reaction. As the chitosan microparticles are utilized for lysis and the nucleic acids do not need to be removed from the microparticles before PCR, the ease of the sample preparation procedure is dramatically improved.

10 Claims, 8 Drawing Sheets
(1 of 8 Drawing Sheet(s) Filed in Color)
Specification includes a Sequence Listing.

Cell lysis using G6PC assay: ~40 bp amplicon
- Mechanical Lysis
  - Optimized for a 3 minute vortex

SINGLE-STEP DNA PREPARATION FOR POLYMERASE CHAIN REACTION USING MAGNETIC CHITOSAN MICROPARTICLES

CROSS-REFERENCE TO RELATED APPLICATION

This application claims the benefit of priority to U.S. Provisional Application No. 62/164,394, filed May 20, 2015, and to U.S. provisional application No. 62/323,188, filed Apr. 15, 2016 the disclosure of which is hereby incorporated by reference in its entirety.

BACKGROUND

1. Field of the Invention

The present invention relates to a method for concentrating a DNA sample for a polymerase chain reaction (PCR). Specifically, the method utilizes magnetic microparticles providing for cell lysis and simultaneous DNA capture in a solution having a PCR compatible pH. Subsequently, the magnetic microparticles serve as a solid support for the DNA template during PCR.

2. Discussion of the Background

Nucleic acid amplification methods are powerful tools for biological research, as well as for disease diagnostics, in particular for genetic and infectious diseases. While the amplification steps are mostly automated, sample preparation can be complex, as DNA or RNA targets are normally diluted in a complex lysate or mixture from food, environmental, or clinical samples. Nucleic acids must be purified prior to amplification because sample DNA can by digested by nucleases, polymerases can be hydrolyzed by proteases, and lysis chemicals can interfere with the amplification reaction.

Figure 1A:
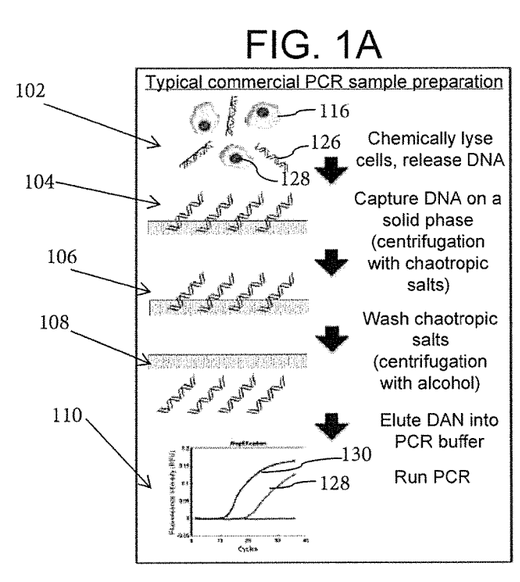
FIG. 1A is a flowchart illustrating a method for concentrating a nucleic acid sample for a PCR reaction according to prior art.

FIG. 1A illustrates a traditional method for purifying nucleic acids in a sample containing cells 116. Nucleic acid purification is carried out using a silica solid phase extraction technique (Boom et al. 1990; D. N. Miller et al. 1999; Haugland, Brinkman, and Vesper 2002). First, in step 102, the cellular sample is lysed with a chemical lysis buffer and agitation to release DNA 126. Then, binding, washing, and elution solutions are driven through a spin column with a silica membrane by centrifugal force in a series of steps. Nucleic acids in samples are denatured by chaotropic salts, such as guanidine hydrochloride, which cause adsorption to the silica in step 104. Alcohol is then used in step 106 to wash away the salts and cellular debris, which would otherwise inhibit PCR. In step 108, purified nucleic acids are eluted off of the silica in a moderate salt buffer and added to the PCR mixture to be amplified in step 110. Curve 130 demonstrates a PCR reaction performed on nucleic acids purified from a biological sample according to steps 102-108.

There are several inherent disadvantages to using silica membranes to purify nucleic acids. For one, typically three to four different solvents are necessary to extract nucleic acids from complex samples. Performing each wash step can be time consuming, while automation of washes increases in complexity with increasing number of solvents. In addition, the chaotropic agents and alcohols required for DNA adsorption to silica are inhibitory to amplification methods. Furthermore, commercial spin columns can process only relatively small samples, for instance on the order of 500 µL. To capture dilute DNA or RNA from a rare target, the sample volume must be increased, leading to volumes that are impractical for spin columns.

Another method for solid phase extraction has been adapted for silica microparticles or microbeads. The surface of the microbeads takes the place of the silica membrane; meanwhile, microbeads enable the elimination of one step from the process by lysing cells and capturing the released DNA under vortex in the presence of a high concentration of chaotropic salts. Nonetheless, even with the elimination of a step, the method is still relatively complex and time consuming.

An additional method that has been reported to reduce the number of sample preparation steps is charge switching. In this approach, nucleic acids are adsorbed onto a pH-responsive material in a moderately low pH (which positively charges the binding surface) and then released into a moderately high pH (compatible with PCR), which neutralizes the binding material. Therefore, in the charge switching methodology, inhibitory salt concentrations, chaotropic salts, or alcohols are not necessary. Previously, DNA capture was only believed possible at pH lower than 7.5, with elution beginning at a pH of 8.0.

Another DNA purification approach is based on employing chitosan in DNA preparation. Chitosan is a particularly useful polycation for charge switching due to its abundance of amine groups that can be charge-modulated via pH. It is a derivative of chitin extracted from crustacean shells and is therefore readily available, inexpensive and biocompatible. The amine group on chitosan has a pKa of about 6.4, hence chitosan is cationic at pH below 6.4 and can readily bind the negatively charged DNA under these conditions. Specifically, chitosan is used as a pH-switchable material which first captures DNA in an acidic buffer and then releases it upon a pH change, for instance to a pH higher than 8.0. The negative phosphate backbone of nucleic acids is electrostatically attracted to chitosan when it is predominately positively charged in buffers below pH 6.4. Silica beads functionalized with low molecular weight chitosan efficiently elute DNA at a moderately high pH (~8.5) compatible with PCR. The use of charge switching implies a reduction in steps (lyse, bind, elute) as compared to silica membranes; however, the number of steps continues to imply complexity in attempts for automation.

Accordingly, there is a need for a method that will reduce the effort required for sample preparation while concentrating the available genomic DNA from a relatively large sample volume down to a small sample volume that is appropriate for PCR.

SUMMARY OF THE INVENTION

In one aspect of the invention, a method of amplifying nucleic acids from a biological sample is provided. Specifically, the method comprises the steps of adding microparticles, optionally magnetic microparticles, to the biological sample and mechanically agitating the biological sample to achieve cell lysis. Next, nucleic acids released from the cells are captured on the microparticles. Subsequently, amplification is performed directly on the captured nucleic acids. In one embodiment, the lysis may be performed by vortexing the biological sample with the microparticles. The microparticles may be fabricated from chitosan. In yet another embodiment, the same buffer is used during both the sample purifiction and amplification. Furthermore, cell lysis in the biological sample may be performed by heating the sample, adding chitosan microparticles, and subsequently vortexing the biological sample. In one embodiment, nucleic acids are selected from the group consisting of: plasmids, bacterial DNA, and human genomic DNA.

In yet another aspect of the invention, a microfluidic system for amplifying nucleic acids from a biological sample is provided. Specifically, the system comprises a lysis unit, a purification unit, and an amplification unit. The lysis unit is configured to mechanically agitate a biological sample combined with microparticles, optionally magnetic microparticles, to lyse cells in the biological sample. The nucleic acids released from the cells are captured on the microparticles. The purification unit is configured to purify the nucleic acids released in the biological sample as result of lysis. Finally, the amplification unit is configured to accept the purified nucleic acids is provided. The amplification is performed directly on the nucleic acids captured on the microparticles. In one embodiment, the lysis may be performed by vortexing the biological sample with the microparticles. The microparticles may be fabricated from chitosan. In yet another embodiment, the same buffer may be used during both the sample purification and amplification. Furthermore, cell lysis in the biological sample may be performed by heating the sample, adding chitosan microparticles, and subsequently vortexing the biological sample. In one embodiment, nucleic acids amplified in the amplification unit are selected from the group consisting of: plasmids, bacterial DNA, and human genomic DNA.

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements. The patent or application file contains at least one drawing executed in color. Copies of this patent or patent application publication with color drawing(s) will be provided by the Office upon request and payment of the necessary fee.

DETAILED DESCRIPTION OF PREFERRED EMBODIMENTS

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The present invention relates to a method for concentrating a nucleic acid sample for a PCR reaction. Specifically, available nucleic acids are concentrated from a relatively large sample volume down to a small sample volume that is appropriate for PCR. The method utilizes microparticles. In one embodiment, the microparticles may be magnetic. In another embodiment, the magnetic microparticles may be fabricated from chitosan. In yet a further embodiment, the microparticles may contain a core coated with chitosan. Those of skill in the art will be able to identify microparticle cores that would be useful in the practice of the present invention, including Si and magnetic compounds.

Chitosan is a polysaccharide poly-[1,4]-β-D-glucosamine that comes commercially in a variety of forms including, but not limited to, mixtures of different weight molecules, which range from about 1,000 daltons to more than 5,000,000 daltons. The amine group on chitosan has a pKa of about 6.4, hence chitosan is cationic at pH below 6.4 and can readily bind the negatively charged DNA under these conditions. Low molecular weights of chitosan (i.e., less than 1,000,000 daltons) efficiently elutes DNA at a moderately high pH (for example, around 8.5) and thus are useful in different embodiments of the present invention, as described in further detail herein. Commercial preparations of chitosan can be used in the practice of the present invention as herein described. In a dense chitosan microenvironment, the pKa can be shifted in the presence of anionic molecules such as nucleic acids. This property is leverged by the present invention to provide adsorption of DNA in a solution that is optimized for PCR and amplification of the DNA while attached to the chitosan.

The chitosan microparticles, fabricated according to the present invention by crosslinking or by coating a Si or magnetic core, provide for cell lysis and simultaneous capture of nucleic acids at a pH optimal for PCR (for example, at pH 8.5) just as efficiently as at low pH. For purposes of the present invention, a high pH refers to a pH level above the pKa of the material used for DNA capture. For chitosan, a high pH would therefore be a pH above 6.4. In some preferred embodiments, a preferred high pH is one at which DNA amplification is possible, such as about 8.0-9.0, and most preferable around 8.5. In addition, for the purposes of the present invention, a low pH refers to a pH level below the pKa of the material described (including as used for DNA capture). For chitosan, a low pH would therefore be a pH below 6.4.

In one embodiment of the present invention, the captured nucleic acids are still accessible by polymerase, such that the microparticles serve as a solid support for nucleic acids amplification in a PCR reaction. Because the microparticles are utilized for lysis, and because the nucleic acids do not need to be removed from the microparticles before PCR, the ease of the sample preparation procedure is dramatically improved.

Furthermore, nucleic acid extraction may be performed on a sample using the same buffer that is used for numerous biochemical reactions, including, but not limited to amplification, including PCR amplification, next generation sequencing, isothermal amplification techniques, aptamer based assays, or enzymatic assays. Extracting DNA with a single buffer may reduce reagents, decrease sample preparation time, and simplify diagnostic systems.

Figure 1B:
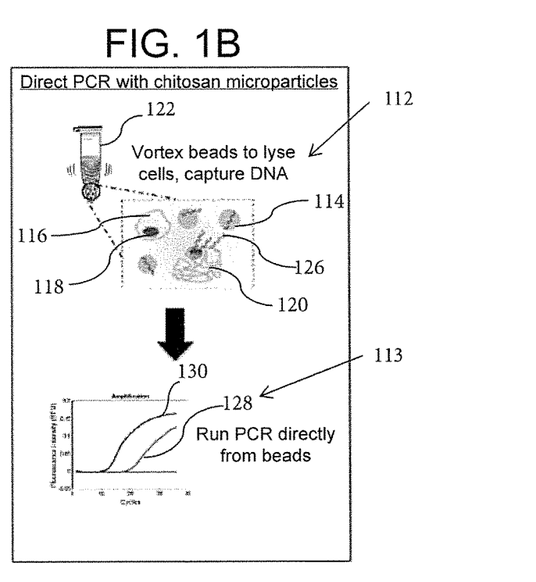
FIG. 1B is a flowchart illustrating a method for concentrating a nucleic acid sample for a PCR reaction according to one embodiment of the present invention.

FIG. 1B is a flowchart illustrating a method for concentrating a nucleic acid sample for a PCR reaction according to one embodiment of the present invention. Specifically, high pH (for instance, pH above the pKa of chitosan, and more preferably from about 8.0 to 9.0) sample solution 124 in a microtube 122 includes cells 116 having a nucleolus 118 containing nucleic acids 126. In step 112, chitosan microparticles 114, hereinafter may be referred to as beads, are added to the sample solution 124 in the microtube 122 and mechanically agitated to lyse the cells 116 in the sample solution 124 and simultaneously capture nucleic acids 126. In one embodiment, the chitosan beads 114 are vortexed. During the vortexing process, the cells 116 are lysed to release nucleic acids 126 from nuclei 118. The nucleic acids 126 are captured on the chitosan beads 114 while cell debris 120 remains in the sample solution. In one embodiment, cross-linked chitosan beads 114 were pre-washed in a high pH buffer. DNA was loaded onto the beads 114 by adding plasmids, bacterial genomic DNA, or hgDNA to the high pH buffer. By way of example, pH 8.5 Tris or pH 8.5 Tris, 0.1% Triton X-100 buffer may be used for capturing DNA on the chitosan beads. Thus, DNA extraction could be performed on a sample using the same buffer that could be used for PCR.

In one non-limiting embodiment, purification of nucleic acids 126 in high pH buffer solution is performed by capturing nucleic acids 126 with chitosan beads 114 in a series of buffer changes. Buffer changes are facilitated by a magnetic tube stand (not shown) that pulls and holds microparticles to one side of the microtube 122. After each buffer change the microtubes 122 are vortexed.

It is within the scope of the present invention that the sample cells may be human cells containing human genomic DNA, plasmids, bacteria or viruses.

In yet another embodiment, sample cells 116 in the microtube may be lysed by heating the microtube. In one non-limiting example, the microtube is heated for 20 minutes. The heating step is followed by adding chitosan beads to the sample and vortexing the sample. Then, the chitosan beads 114 are separated from the sample and washed.

Figure 1C:
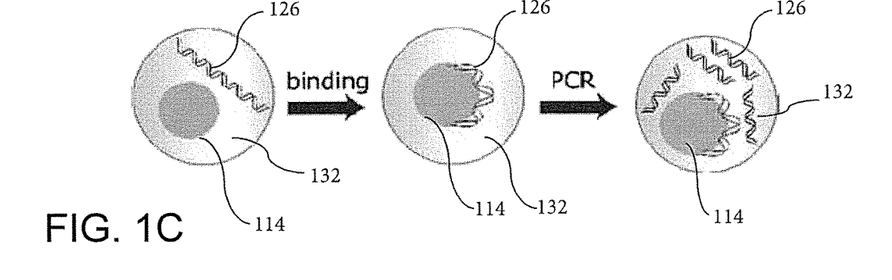
FIG. 1C is a diagram illustrating DNA purification and amplification process according to one embodiment of the present invention.

Next, in step 113, a reaction mixture comprising forward and reverse primers and fluorescence dyes may be added to the nucleic acids 126 captured on the beads 114. A PCR reaction is performed to amplify the nucleic acids 126 attached to the chitosan beads 114. As shown in FIG. 1C, nucleic acids 126 captured on chitosan beads 114 are amplified without release and in the same high-pH buffer 132 used for lysis and purification. Plasmids, bacterial, and hgDNA can be amplified by using the method according to the present invention.

Returning to FIG. 1B, curves 128 and 130 represent fluorescence intensity, RFU, at each cycle of two PCR reactions. The PCR reaction represented by the curve 128 is a PCR reaction performed directly from the chitosan beads according to the current invention. The PCR reaction represented by the curve 130 is a PCR reaction performed on nucleic acids not attached to chitosan beads as described in FIG. 1A.

Figure 11:
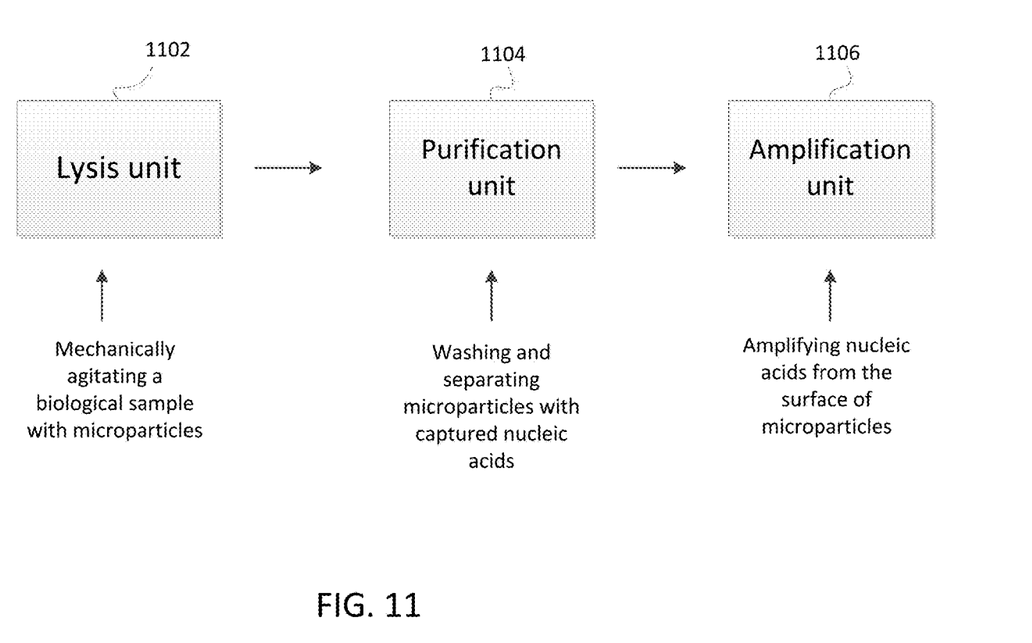
FIG. 11 is a diagram illustrating a system for concentrating a nucleic acid sample for a PCR reaction according to FIG. 1B.

FIG. 11 illustrates a system for amplifying nucleic acids from a biological sample. Specifically, a lysis unit 1102, a purification unit 1104, and an amplification unit 1106 are provided to perform the steps of the method according to FIG. 1B. The lysis unit 1102 is configured to mechanically agitate the biological sample combined with beads (microparticles) to lyse cells in the biological sample. Examples of lysis units include variable speed vortexers, which provide vortexing at a range of low, medium and high speeds. The specific rpm that defines low, medium and high will be dependent on the specific unit used, and such settings will be easily determined by those of skill in the art. At the same time as the lysis unit 1102 causes the cells to lyse, nucleic acids released from the cells are captured on the magnetic beads. The purification unit 1104 is configured to purify the nucleic acids released in the biological sample as result of lysis by separating and washing beads with captured nucleic acids according to step 112 of FIG. 1B. Finally, the amplification unit 1106 is configured to accept the purified nucleic acid to perform amplification directly on the captured nucleic acids according to step 113 of FIG. 1B.

By way of non-limiting example, the reaction mixture used for amplification of nucleic acids captured on the chitosan beads in the amplification unit 1106 may comprise a dye, including, but not limited to SYBR Green, and forward and reverse primers.

Dyes that may be useful in the practice of the present invention include those that intercalate within strands of nucleic acids. The classic example of such a dye is ethidium bromide. An exemplary use of ethidium bromide for binding assays includes, for example, monitoring for a decrease in fluorescence emission from ethidium bromide due to binding of test molecules to nucleic acid target molecules (ethidium bromide displacement assay). See, e.g., Lee, M. et al. (J Med Chem 36(7):863-870 (1993)). The use of nucleic acid intercalating agents in measurement of denaturation is well known to those in the art. See, e.g., Haugland (Handbook of Fluorescent Probes and Research Chemicals, Molecular Probes, Inc., Eugene, Oreg. (1996)). Dyes that bind to nucleic acids by mechanisms other than intercalation can also be employed in embodiments of the invention. For example, dyes that bind the minor groove of double stranded DNA can be used to monitor the molecular unfolding/denaturation of the target molecule due to temperature. Examples of suitable minor groove binding dyes are the SYBR Green family of dyes sold by Molecular Probes Inc. (Eugene, Oreg., USA). See, e.g., Haugland (Handbook of Fluorescent Probes and Research Chemicals, Molecular Probes, Inc., Eugene, Oreg., USA (1996)). SYBR Green dyes will bind to any double stranded DNA molecule. When a SYBR Green dye binds to double stranded DNA, the intensity of the fluorescent emissions increases. As more double stranded DNA are denatured due to increasing temperature, the SYBR Green dye signal will decrease. Another suitable dye is LCGreen Plus sold by BioFire Technology, Inc.

Following a high-pH (for instance pH of about 8.5) capture, the beads (microparticles) may be re-suspended in a high pH loading buffer and transferred to a PCR well. The loading buffer may be replaced with the reaction mixture and then aspirated via pipette. In one non-limiting embodiment, bubbles in the wells are removed by centrifugation. A magnet may be used to disperse microparticles throughout the well after centrifugation and to ensure they are not tightly packed at the bottom. Magnets may be placed adjacent to wells during PCR, which may hold microparticles to one side of a well and allowed for real time fluorescent measurements.

Figure 2:
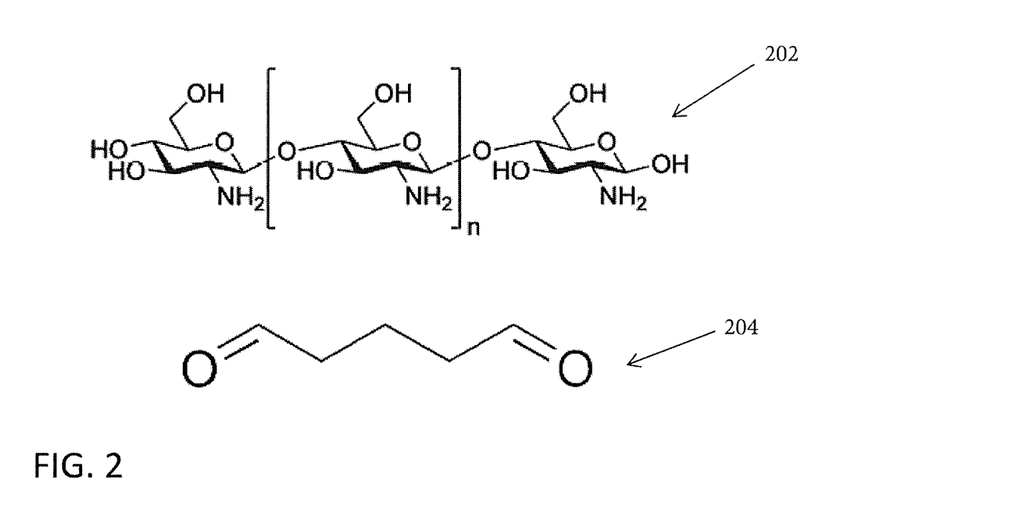
FIG. 2 presents chemical structures of chitosan (top) and glutaraldehyde (bottom).

According to an exemplary embodiment of the present invention, chitosan beads (microparticles) used for capturing nucleic acids are fabricated by creating chitosan droplets in oil and then crosslinking the droplets into microparticles. Aldehydes readily react with amines to form labile Schiff bases. Thus, intermolecular and intramolecular bonds between chitosan amine groups are formed when exposed to glutaraldehyde as shown in FIG. 2. Specifically, chitosan droplets may be cross-linked into microparticles by reacting chemical structures of chitosan (202) and glutaraldehyde (204). These bonds are reduced to covalent bonds with a reducing agent such as NaBH4. These reactions may be utilized by immersing aqueous chitosan droplets in glutaraldehyde-laden oil. Thus, the droplets are cross-linked into microparticles, where the cross-linking reaction starts at the oil-water interface and continues into the core of a microparticle over time. The outer surface of the chitosan microparticles is charge switchable, but the interior of the microparticle, beneath this charge-switchable shell, remains positively charged. DNA is captured below the inner shell due to aggressive mechanical agitation that is necessary for the initial cell lysis, yet the DNA is still accessible to polymerase for amplification.

By way of non-limiting example, the process of fabrication chitosan microparticles utilizes stock solutions of low molecular weight chitosan as previously described in acetic acid and an oil solution of Span 80 in hexadecane that are prepared and stored at room temperature. Prior to microparticle fabrication, an aqueous solution of low molecular weight chitosan and magnetic iron (III) oxide nanoparticles in acetic acid was prepared. The iron (III) oxide nanoparticles are used to provide the magnetic core of the chitosan microparticles. Other magnetic materials may also be used, as would be known to one of skill in the art. Chitosan was emulsified in a beaker by dripping of the aqueous solution into the oil solution under constant mixing with a homogenizer. After emulsifying, the crosslinking mixture was added dropwise and then further mixed with the homogenizer. Microparticles are cross-linked by glutaraldehyde reacting with chitosan amine groups to form Schiff bases. Next, the microparticles are transferred to a tube and cross-linked for a desired amount of time on a nutator. The crosslinking reaction may be stopped by removing the glutaraldehyde-laden hexadecane after the microparticles have been centrifuged.

To prepare the microparticles for DNA adsorption assays, the microparticles are first washed twice with the oil solution. Then the microparticles are resuspended in the oil solution and dried out with an air stream bubbling through the solution overnight. The oil solution is removed by washing the microparticles twice, first in decanol, then ethanol, and finally 10 mM Tris. The Schiff bases that cross-linked the microparticles are then reduced to secondary amines. After reduction, the microparticles are washed. Finally, they are dried at room temperature under vacuum. The microparticles are stored in 10 mM Tris.

Figure 3A:
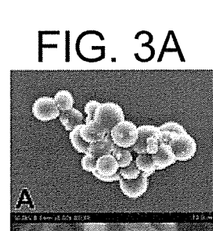
FIG. 3A-C presents SEM images of chitosan microparticles.
Figure 3B:
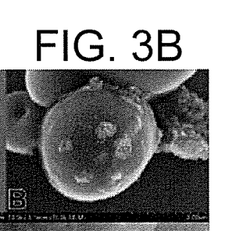
Figure 3C:
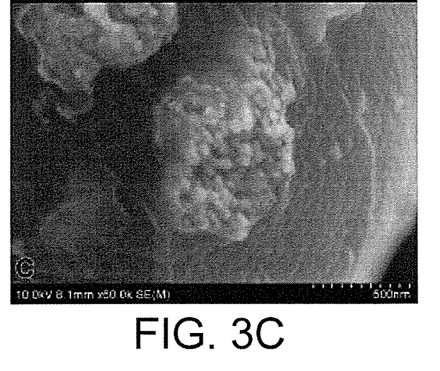

FIG. 3 illustrates scanning electron micrographs (SEM) of the chitosan microparticles fabricated according to the exemplary embodiment of the present invention described with the reference to FIG. 2. Images acquired during cross-linking, washing, and drying in hexadecane show dispersed microparticles. However the microparticles are aggregated into larger particles when washed with solvents other than hexadecane. Furthermore, large clumps of microparticles may be formed after drying under vacuum, which were broken down by sonication.

FIG. 3 includes SEM images of the final freeze dried chitosan microparticle product showing individual microparticles clustered into larger particles. Specifically, FIG. 3A shows individual narrowly polydisperse microparticles ranging in diameter from 0.5 to 8 µm. A large majority of the microparticles is clustered into particles on the order of 10 µm. FIG. 3B illustrates a cluster of microparticles with iron(III) oxide nanoparticles, 20 to 40 nm in diameter. The microparticles are very responsive to magnets in close proximity, which allowed for quick buffer changes. FIG. 3C is a magnified view of iron(III) oxide nanoparticles embedded within the chitosan matrix of the microparticle.

Accordingly, the core of the microparticles maintains a positive charge at PCR compatible pH, thus retaining genomic DNA captured under vortex conditions. The method according to the present invention has a potential to completely eliminate manual steps (or robotic replications) using magnetic microparticles densely coated with the polycationic polymer chitosan. The magnetic microparticles according to the present invention are capable of lysing cells through mechanical agitation. Simultaneously, the dense layer of chitosan electrostatically captures nucleic acids released during lysis. Even at pH above the pKa of chitosan, microparticles with a high density of chitosan retain their capability to electrostatically bind. DNA amplification can be performed immediately following capture without the need for removing lysis agents, chaotropic salts, and alcohols, as is typically done in conventional PCR sample preparation. As a result, one can perform amplification of nucleic acids including, but not limited to, plasmids, bacterial DNA, and hgDNA in a simple two-step process of lysis and direct PCR.

In yet in another alternative embodiment, chitosan coated silica microparticles may be used to capture nucleic acids while performing mechanical lysis to release DNA from cells. Similar to cross-linked chitosan microparticles, the chitosan coated silica microparticles may be used to serve as a solid support for the DNA template during PCR.

To summarize, the present invention is directed to a method and system for amplifying nucleic acids from a biological sample. Specifically, microparticles are added to the biological sample. The biological sample having the microparticles is mechanically agitated to achieve cell lysis. Next, nucleic acids released from the cells in the biological sample are captured on the microparticles. The nucleic acids are may be one of: plasmids, bacterial DNA, and hgDNA. Subsequently, amplification is performed directly on the captured nucleic acids in that microparticles serve as a solid support for a DNA template during amplification.

In one embodiment, the cell lysis in the biological sample may be performed by vortexing the biological sample with the microparticles. In yet another embodiment, the cell lysis may be performed by heating the biological sample, adding chitosan microparticles, and subsequently vortexing the biological sample.

The microparticles may be fabricated from chitosan. The interior of a chitosan microparticle, beneath a charge-switchable shell, remains positively charged at high pH. In one embodiment, the chitosan particles are fabricated by creating chitosan droplets in oil and then crosslinking the droplets into microparticles. The crosslinking begins at the oil-water interface and continues into the core of the microparticle over time. Next, the microparticles are washed twice with the oil solution, resuspended in the oil solution, and dried out with an air stream bubbling through the solution. The oil solution is removed by washing the microparticles twice.

In one embodiment, the biological sample has a PCR amplification compatible pH. Sample purification may be performed with the same buffer as the amplification. In one embodiment, purification may include separating and washing microparticles with captured nucleic acids.

In yet another embodiment, microparticles are magnetic microparticles. Specifically, magnetic nanoparticles may be embedded within individual microparticles. In one exemplary embodiment, the nanoparticles are iron nanoparticles measuring 20-40 nm in diameter.

Example 1

DNA Capture with Chitosan Microparticles

It is well known in the art that chitosan captures DNA efficiently at moderately low pH because it is positively charged. In one non-limiting embodiment of the present invention, DNA capture assays were performed by a series of buffer changes in microtubes. Buffer changes were facilitated by a magnetic tube stand that pulled and held microparticles to one side of the tubes. Supernatants were saved for qPCR analysis. After each buffer change the tubes were vortexed at the highest speed for 3 minutes. Low pH DNA adsorption assays were carried out by prewashing 40 µg of chitosan microparticles cross-linked for 30 minutes twice in low pH load buffer (pH 6, 10 mM MES, 0.1% Triton X-100). DNA was loaded onto the microparticles by adding 99 µL of low-pH load buffer and 1 µL of pUC19 plasmid DNA diluted in DI $H_2O$. Then the microparticles were washed in 100 µL of low-pH load buffer. Lastly, the microparticles were vortexed in 100 µL elution buffer (pH 9, 10 mM Tris, 0.1% Triton X-100 and 50 mM KCl). The amount of DNA in the supernatant of each step was quantified with qPCR. Reactions consisted of 10 µL of iQ SYBR Green Supermix, 2 µL of 2.5 µM forward primer (GTC TCATGA GCG GAT ACA A) (SEQ ID NO: 2), 2 µL of 2.5 µM reverse primer (CTC GTG ATA CGC CTA TTT TT) (SEQ ID NO: 3) and 6 µL of samples. Reactions were hot started at 95° C. for 3 minutes followed by 30 thermal cycles. Each cycle consisted of a melt step at 95° C. for 3 s and an anneal step at 56° C. for 30 s. Serial dilutions of plasmid pUC19 in load and elution buffers were used to make a calibration curve and quantify unknown samples. Calibration curve is constructed by plotting the log of starting quantity of template against threshold cycle, Ct, defined as the number of cycles it took to detect a real signal from a sample.

As expected, the qPCR results proved that the chitosan microparticles efficiently captured DNA from acidic buffers. However, the whole chitosan microparticles did not elute DNA at a high pH as had been demonstrated with solid supports functionalized with oligomeric chitosan. Also, further washing the microparticles with elution buffer multiple times did not result in pUC19 in solution.

It was attempted to elute DNA off the microparticles at more extreme elution conditions by increasing the ionic strength, increasing the pH, and increasing the temperature by subjecting the microparticles to 30 PCR thermal cycles including a hot start step. These tests were performed after microparticles were loaded with pUC19 and washed to test the adsorption capability of the microparticles. Additional washes with elution buffer were performed to increase the probability of eluting DNA. High ionic strength conditions were examined by vortexing microparticles in 100 µL of pH 8.5, 10 mM Tris, 0.1% Triton X-100, and up to 500 mM KCl for 3 minutes. High pH conditions were examined by vortexing microparticles in Tris, bicarbonate, or sodium hydroxide buffers at a concentration of 10 mM and up to pH 12.5 for 3 minutes. High temperature elution was examined by suspending the microparticles in 100 pLL of elution buffer and thermal cycling them following the qPCR protocol. The DNA eluted into the buffer was quantified with qPCR.

None of the enhanced elution conditions resulted in free DNA that could be measured via qPCR. This indicated that extreme elution conditions did not diminish the interactions between the whole chitosan microparticles and DNA and that the interaction was strong. Since the DNA chitosan interaction was preserved at high pH, it was attempted to capture DNA at pH 8.5. High pH DNA adsorption assays were similar to low pH assays. First, 40 µg of chitosan microparticles were prewashed twice in high-pH loading buffer; pH 8.5, 10 mM Tris, 0.1% Triton X-100. DNA was loaded onto the microparticles by adding 99 µL of high pH load buffer and 1 µL of pUC19 diluted in DI H2O. Lastly, the microparticles were washed in 100 µL of high pH load buffer. The amount of DNA in the supernatants at each step was quantified with qPCR.

Figure 6:
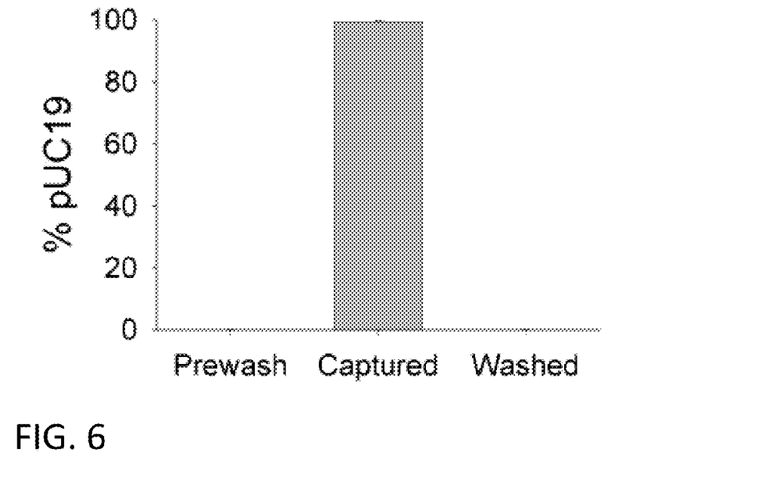
FIG. 6 is a histogram illustrating extraction of copies of pUC19 plasmid DNA at pH 8.5.

Capture of pUC19 in a pH 8.5 Tris buffer using chitosan microparticles was just as efficient as at low pH. FIG. 6 shows that no DNA was found in the solution after chitosan microparticle capture, and no DNA was found in the microparticle washing solution. Specifically, FIG. 6 shows that extraction of 10 copies of pUC19 plasmid DNA (SEQ ID NO: 1) at pH 8.5. All of the DNA was captured and could not be eluted or washed off, using only a pH 8.5 buffer of 10 mM Tris and 0.1% Triton X-100. It appears that 100% of the DNA was captured. DNA captured onto chitosan at high pH is significant because nucleic acid assays are performed at pH around 8.5. This example demonstrates that DNA extraction can be performed on a sample using the same buffer that is used for nucleic acid assays including PCR, next generation sequencing, isothermal amplification techniques, aptamer based assays, or enzymatic assays.

Example 2

Amplifying DNA Directly from the Chitosan Microparticles

Figure 7:
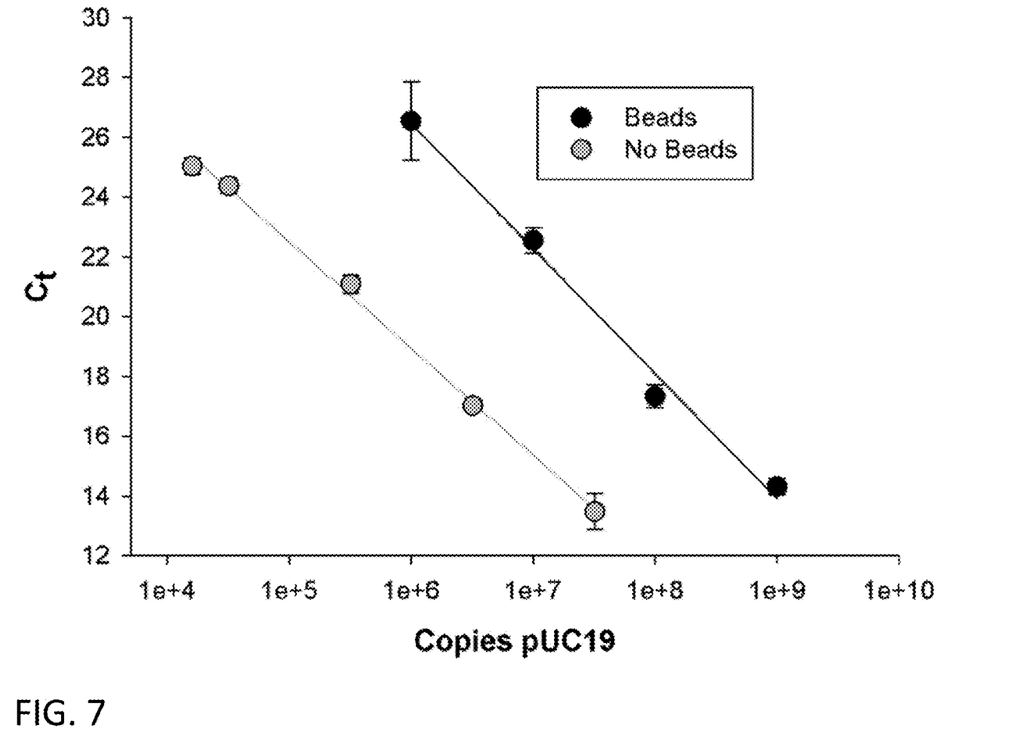
FIG. 7 presents pUC19 PCR calibration curves for reactions utilizing microparticles (black circles) and reactions without microparticles (gray circles).
Figure 8:
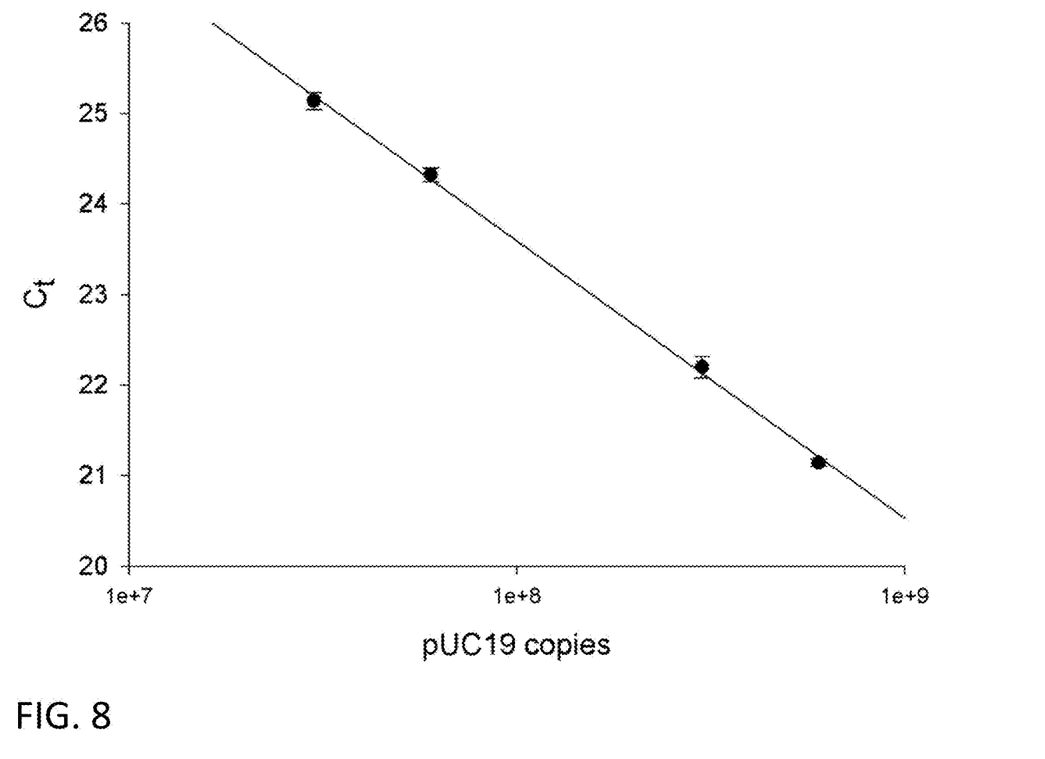
FIG. 8 presents a PCR calibration curve for pUC19 plasmid constructed from primers aspirated with chitosan microparticles cross-linked for 0.5 hour.

Based on the method according to the present invention, plasmid DNA captured onto the chitosan microparticles can be amplified via PCR without release. By way of non-limiting example, the reaction mixture may consist of 1×iQ SYBR Green Supermix, 0.36 nM forward primer, and 0.36 nM reverse primer. Following a high-pH capture, the microparticles were re-suspended in 30 µL of high pH loading buffer and transferred to a PCR well. The loading buffer was replaced with 20 µL of reaction mixture and then aspirated via pipette. Real-time PCR results are presented in FIG. 7. Specifically, FIG. 7 demostrates PCR calibration curves for PCR reactions performed with microparticles (black circles) and PCR reactions performed without microparticles (gray circles). Addition of chitosan microparticles into the reaction resulted in less efficient PCR, E=67.6%, than reactions without microparticles, E=90.6%. However, to successfully amplify DNA off the microparticles, the concentrations of enzyme and primers were slightly increased. The PCR products were verified by melt (denaturation) analyses and gel electrophoresis. The melt analysis was conducted immediately after a microparticle PCR with the same thermal cycler. The temperature was increased from 65 to 95° C. every 5 s by 0.5° C. and the fluorescence was measured at each temperature step. Also, the microparticle PCR supernatant was run on a 1% agarose and 1.6×SYBR Green I gel at 75 V for 1.5 hrs. The calibration curve was constructed from standard samples of pUC19, and found to be linear over 4 orders of magnitude. Although the plasmid DNA amplified, the efficiency of PCR was diminished to 67.6% as opposed to 90.6% as seen in reactions with the same concentration of enzyme and primers but without microparticles. The decrease in PCR efficiency with the addition of chitosan microparticles to the reaction could possibly be attributed to primer and/or amplicon adsorption during the reaction. Primer adsorption was measured by performing PCR reactions with the supernatant of a primer solution that was mixed with chitosan microparticles. First, 40 µg of chitosan microparticles cross-linked for 30 minutes. were prewashed twice in high-pH loading buffer. Then 100 µL of 10 mM Tris, 2.5 µM forward primer, 2.5 µM reverse primer and 0.1% Triton X-100 at pH 8.5 was aspirated with the microparticles via pipette. The primer solution was removed and used for real time PCR (qPCR). Reaction mixtures consisted of 10 µL iQ SYBR Green Supermix, 2 µL of primer solution, 2 µL DI H$_2$O, and 6 µL of pUC19 standards. Solutions vortexed with the microparticles for 3 minutes did not amplify DNA. However, aspirating with a pipette, not vortexing, is normally used to mix PCR reactions in wells. Solutions aspirated with the microparticles by pipette efficiently amplified pUC19 indicating the gentler mixing prevented DNA from effectively penetrating and absorbing onto (or into) the microparticles. FIG. 8 presents a PCR calibration curve constructed from primers aspirated with chitosan microparticles cross-linked for 0.5 hr. The efficiency of the reaction was 112%, therefore minimal primers were absorbed. Amplicon adsorption was measured by aspirating diluted samples of thermal cycled PCR reactions with chitosan microparticles and using qPCR to measure amplicons left in solution. First, 40 µg of chitosan microparticles were prewashed twice in high pH loading buffer. Amplicons were loaded onto the microparticles by adding 99 µL of high-pH load buffer and 1 µL of amplicons diluted in DI H$_2$O. The microparticles were not vortexed; instead they were aspirated via pipette. The amplicons added were produced from a standard pUC19 PCR used to create a calibration curve and diluted by a factor of $10^4$ or $10^6$. DNA that remained in the supernatant was quantified with qPCR and an amplicon calibration curve. Half of the amplicons added to the microparticles were captured, even with gentle mixing. Since amplicons absorbed more easily than primers, PCR efficiency of reactions with microparticles was lost due to amplicons being absorbed as they were polymerized. It may be possible to recover PCR efficiency by measuring fluorescence increases directly on the chitosan microparticles instead of in solution.

Example 3

Investigating the Mechanism of High-pH Capture

To investigate the mechanism of DNA adsorption to chitosan microparticles at high pH, the adsorption of an anionic dye, brilliant yellow (BY), was measured as a function of pH. Solutions of BY in 10 mM buffers and 0.1% Triton X-100 from pH 5 to 12.5 were made as standards and load samples. First, 40 µg of chitosan microparticles were prewashed twice in buffer without BY. Then 100 µL of 50 uM BY was loaded onto the microparticles. After vortexing for 3 minutes, BY remaining in the supernatant was quantified by comparing the absorbance at 397 nm with an Evolution 60 spectrophotometer to standard solutions. The adsorption of methylene blue (Sigma) and gold nanoparticles to chitosan microparticles cross-linked for 0.5 hour. (absorbance measured at 670 nm and 530 nm respectively) was also measured at pH 6 and pH 8.5.

Figure 9:
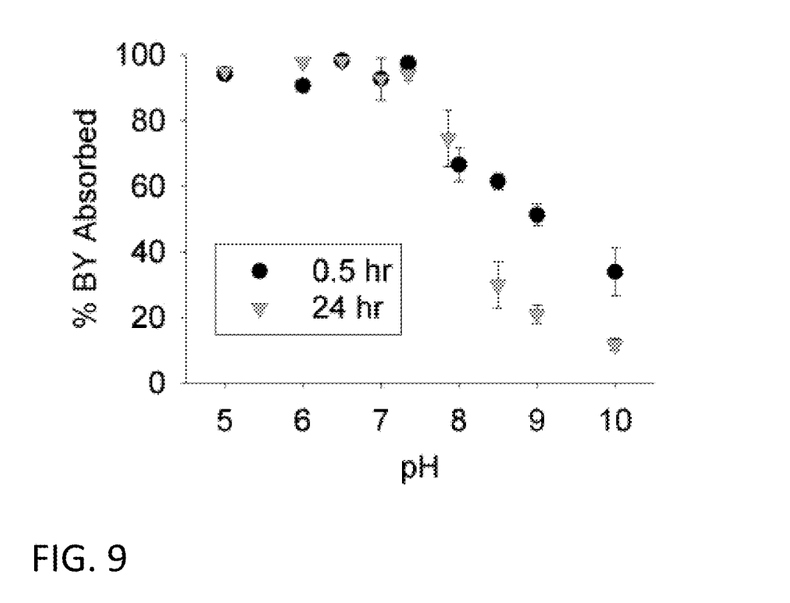
FIG. 9 demonstrates adsorption of brilliant yellow dye onto chitosan microparticles cross-linked for 0.5 hour (black circles) and 24 hours (gray inverted triangles).

It was found that chitosan microparticles were still pH responsive because they captured nearly 100% of the added dye below pH 7.5, while above pH 7.5 BY adsorption decreased. FIG. 9 shows adsorption of brilliant yellow dye onto chitosan microparticles cross-linked for 0.5 hour (black circles) and 24 hour (gray inverted triangles). The pH response was enhanced by cross-linking the microparticles for 24 hour, and at pH greater than 8 significantly less BY was absorbed than for the 0.5 hour cross-linked microparticles. Increased cross-linking reacted away protonable chitosan amine groups, which would limit possible electrostatic interactions. The amount of BY absorbed as a function of pH also indicated the pKa of chitosan amines shifted higher from 6.4 to about 7.5. The adsorption of methylene blue, a cationic dye, to the chitosan microparticles was also investigated. There was neither significant adsorption nor a change in adsorption due to pH, confirming the interaction was charge specific. Most likely, positive charges within the chitosan microparticle were interacting with negatively charged BY and DNA. Furthermore, the adsorption of negatively charged gold nanoparticles, 40-50 nm in diameter, was investigated. At pH 6, 20% of nanoparticles added were absorbed compared with only 5% of the nanoparticles absorbed at pH 8.5. Significantly fewer gold nanoparticles were absorbed at low pH than BY because of the size difference. Gold nanoparticles were not be able to penetrate into a crosslinked chitosan matrix of embedded iron nanoparticles. Instead, they would be restricted to the outer surface of the microparticles, which would limit the number of protonated amines available. Additionally, the limited unreacted amines on the outer surface of the microparticles would be uncharged at pH 8.5, leading to the decrease in adsorption. Charged amine groups within chitosan microparticles enabled efficient adsorption of DNA at high pH and the microenvironment within the microparticles shifted the pKa the amine groups. Ma, et al. ("New Insights into Chitosan-DNA Interactions Using Isothermal Titration Microcalorimetry," Biomacromolecules, 10, 1490-1499, 2009), measured the degree of protonated chitosan at pH 7.4 in chitosan-DNA complexes and found it was equal to chitosan in solution at pH 5.5. The reported pKa of chitosan amines, 6.4, is valid for dilute aqueous solutions, but it is not valid within a dense chitosan mesh with other immediately surrounding amine groups and a difference in electrostatic potential.

Furthermore, additions of negatively charged molecules in the microenvironment dramatically changed the electrostatic potential and made it favorable for amines groups within the microparticles to become charged. It is believed that pUC19 DNA penetrated a small depth into the microparticles and was electrostatically and sterically bound to the microparticles. The microparticles were produced by initially cross-linking chitosan on the outer surface and over time reacting inwards to the core of the microparticle.

Figure 10:
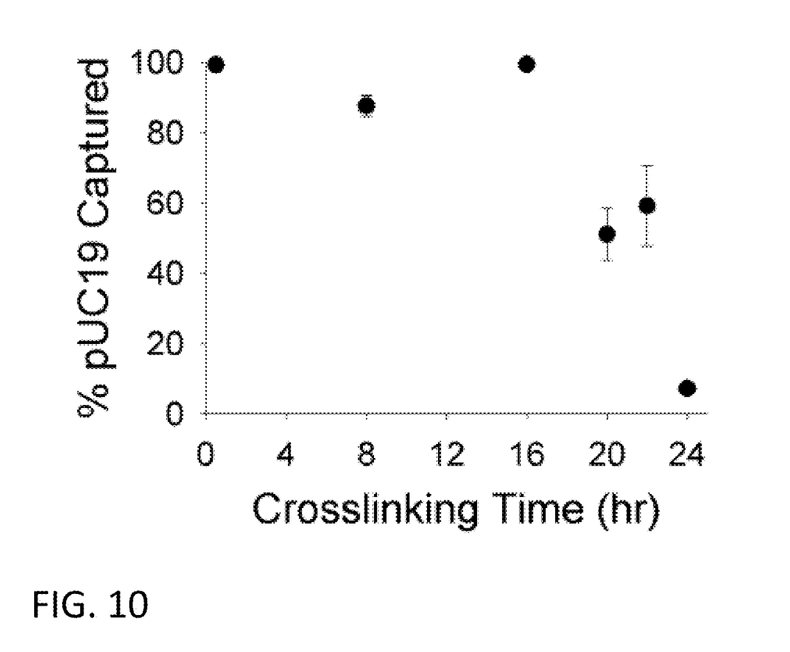
FIG. 10 demonstrates capture efficiency of pUC19 plasmid as a function of cross-linking time.

Therefore, as microparticles were cross-linked for longer times, the thickness of the shell of reacted amines around the microparticle increased. DNA adsorption occurred through electrostatic interactions with protonable amines within the microparticle, and a large shell thickness of reacted amines would diminish the interaction. The decrease in capture efficiency of pUC19 was shown as a result of increasingly cross-linked chitosan microparticles. FIG. 10 shows capture efficiency of pUC19 as a function of cross-linking time. Over time an appreciable shell of amines were cross-linked around the chitosan microparticle and pUC19 was not adsorbed. The efficiency remained high up to 16 hours of cross-linking. Cross-linking longer, up to 22 hours, resulted in about 50% pUC19 capture and with 24 hours of cross-linking, pUC19 capture was reduced to 7%. The shell of unreacted amines after cross-linking for 16 hours was too thick for pUC19 to easily penetrate into the microparticles and adsorb. Further cross-linking increased the shell thickness to the point that the distance of DNA to penetrate into the microparticle was infeasible and pUC19 DNA remained in solution.

Example 4

The process of fabrication chitosan microparticles utilizes stock solutions of 2% (weight per weight (w/w)) low molecular weight chitosan as previously described in 2% (volume per volume (v/v)) acetic acid and an oil solution of 2% (w/w) Span 80 in hexadecane that are prepared and stored at room temperature. Prior to microparticle fabrication, an aqueous solution of 1% (w/w) low molecular weight chitosan and 0.5% (w/w) magnetic iron (III) oxide nanoparticles in 1% (v/v) acetic acid; and a crosslinking mixture of 0.44 g gluataraldehyde (grade 1, 70% in $H_2O$, Sigma) in oil solution are prepared. Chitosan was emulsified in a 100 mL beaker by dripping 1 mL of the aqueous solution into 19 mL of the oil solution under constant mixing with a homogenizer set at 1600 rpm. After emulsifying for 3 minutes, the crosslinking mixture was added dropwise and then further mixed with the homogenizer an additional 5 minutes. Microparticles are cross-linked by glutaraldehyde reacting with chitosan amine groups to form Schiff bases. Next, the microparticles are transferred to a 50 mL tube and cross-linked for a desired amount of time on a nutator. The crosslinking reaction may be stopped by removing the glutaraldehyde-laden hexadecane after the microparticles have been centrifuged at 1000 rpm for 2 min.

To prepare the microparticles for DNA adsorption assays, the microparticles are first washed twice with the oil solution. Then the microparticles are resuspended in the oil solution and dried out with an air stream bubbling through the solution overnight. The oil solution is removed by washing the microparticles twice, first in decanol, then ethanol, and finally 10 mM Tris. The Schiff bases that cross-linked the microparticles are then reduced to secondary amines in 1%/(w/w) NaBH4 in 10 mM Tris overnight. After reduction, the microparticles are washed twice in 10 mM Tris. Finally, they are dried overnight at room temperature under vacuum. The microparticles are stored in 10 mM Tris at a concentration of 40 mg/mL at 4° C.

Example 5

Figure 4A:
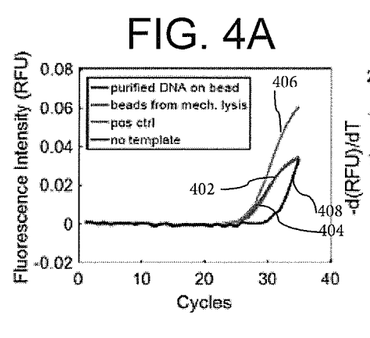
FIG. 4A demonstrates amplification curves of direct PCR with purified DNA on beads and DNA from human cell lysates, in comparison to positive control amplification curves FIG. 4B demonstrates denaturation curves of amplicons produced in experiment shown in FIG. 4A.

FIG. 4A relates to real time PCR amplification of purified hgDNA obtained from MCF7 human breast cancer cells according to the present invention. Amplification curves in FIG. 4A represent fluorescence intensity, (shown in relative fluorescence units or RFU), at each PCR cycle for a plurality of different samples. Purified MCF7 DNA attached to chitosan beads is amplified directly from the surface of the chitosan beads. Amplification curve 402 confirms purified MCF7 DNA amplification performed directly from the beads surface. Amplification curve 404 relates to amplification of MCF7 DNA attached to chitosan beads by mechanically agitating the MCF7 sample solution with the chitosan beads to lyse MCF7 cells and extract MCF7 DNA. Specifically, MCF7 DNA is captured on chitosan beads by vortexing chitosan beads with the MCF7 sample solution. Curve 406 is an amplification curve for positive control purified MCF7 DNA amplified from a solution by a traditional technique without using chitosan beads. Curve 408 is a non-template control curve that allows for monitoring contamination and primer-dimer formation. The amplification was performed by using Glyceraldehyde-3-phosphate dehydrogenase (GAPDH) primer set to produce 600 base pair (bp) long amplicons. Amplification curves 402 and 404 confirm amplification of purified MCF7 DNA performed directly from the beads surface according to the present invention.

Figure 4B:
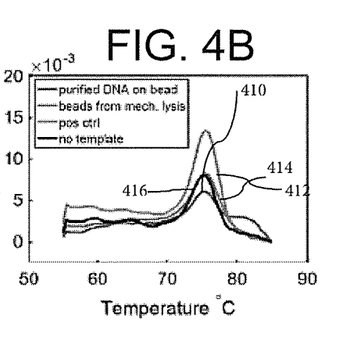

The PCR products can be verified by analyzing denaturation curves in FIG. 4B and/or performing gel electrophoresis (not shown). Turning to FIG. 4B, denaturation curves in FIG. 4B corresponding to amplification curves in FIG. 4A are provided as negative derivative plots of denaturation curves, −d(RFU)/dT, for a plurality of different DNA samples, wherein RFU is the fluorescence intensity measured as the sample temperature T is continuously increasing, resulting in DNA denaturation. Denaturation curve 410 corresponds to the purified MCF7 DNA amplification curve 402. Denaturation curve 412, corresponding to the amplification curve 406, is a denaturation curve for positive control MCF7 DNA amplified from a solution according to a traditional technique without using chitosan beads. Denaturation curve 414, corresponding to amplification curve 404, is a denaturation curve for MCF7 DNA attached to chitosan beads by mechanical agitation and amplified from the surface of chitosan beads according to the present invention. Denaturation curve 416 corresponds to the non-template curve 408. Notably, the melt temperatures of amplicons from both bead samples (curves (402, 410) and (404, 414)) match those of positive control sample (curves 406, 412). Accordingly, DNA amplification process according to the present invention produces the same amplicons (charackterized by the same melt temperature) as the amplicons produced by traditional amplification techniques.

Example 6

Figure 5A:
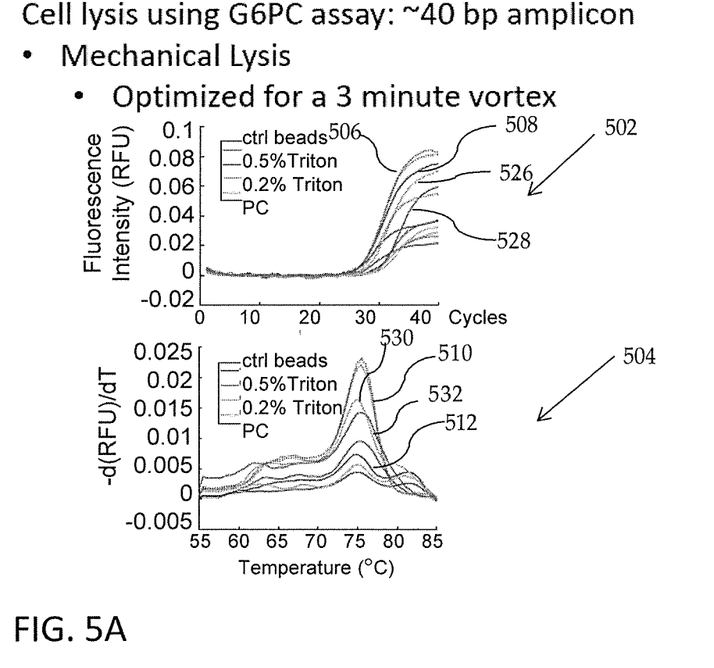
FIGS. 5A and 5B present amplification and denaturation curves for PCR reactions performed on hgDNA according to a second embodiment according to another embodiment of the present invention.
Figure 5B:
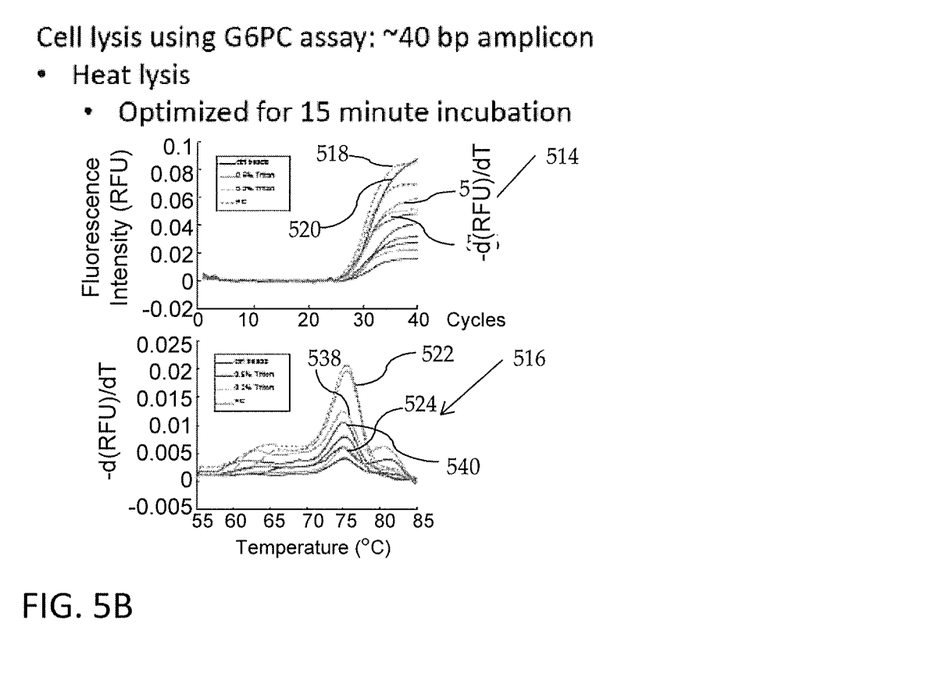

FIGS. 5A-B demonstrate amplification curves (502 and 514) and corresponding denaturation curves (504 and 516) for purified hgDNA obtained from MCF7 human breast cancer cells and amplified by using G6PC primers to produce 40 bp amplicons.

In FIG. 5A, MCF7 human breast cancer cells were lysed by vortexing the sample solution with the chitosan beads at moderate speed. After vortexing, the chitosan beads were separated from the solution and then washed at low speed. As result of the lysis process, MCF7 DNA is captured on the chitosan beads. The lysis process according to the present example was optimized for 3 minute vortex.

Amplification curves 502 relate to amplification of purified MCF7 DNA and represent fluorescence intensity at each PCR cycle for a plurality of different samples. Specifically, curve 508 is an amplification curve for purified MCF7 DNA captured and amplified from the chitosan beads. Curve 506 is an amplification curve for positive control (PC) purified MCF7 DNA amplified from a solution without using chitosan beads. Curves 526 and 528 are amplification curves showing amplification of purified MCF7 DNA amplified from the surface of chitosan beads in 0.5% and 0.1% Triton solution, respectively.

Denaturation curves 504 corresponding to amplification curves 502 are provided as negative derivative plots of denaturation curves, −d(RFU)/dT, for a plurality of different DNA samples. Curves 510 are denaturation curves for PC MCF7 DNA amplified from a solution without using chitosan beads. Denaturation curve 512, corresponding to amplification curve 508, is a denaturation curve for purified MCF7 DNA amplified from the surface of chitosan beads according to the present invention. Curves 530 and 532 are denaturation curves of MCF7 DNA amplified from the surface of chitosan beads in 0.5% and 0.1% Triton solutin, respectively.

In contrast to FIG. 5A, FIG. 5B relates to amplification of purified MCF7 DNA using the same primer set as in FIG. 5A, but a different concentration process. Specifically, curves 514 relate to PCR amplification performed on samples concentrated in a process starting with heat lysis. In the present example, heat lysis is optimized for 15 minutes incubation. In the next step, chitosan beads are added to the sample and vortexed at low speed. Subsequently, the beads are separated and washed at low speed. Curve 518 is an amplification curve for PC MCF7 DNA amplified from a solution without using chitosan beads. Curve 520 is an amplification curve for purified MCF7 DNA captured and amplified on chitosan beads. Curves 534 and 536 are amplification curves showing amplification of purified MCF7 DNA amplified from the surface of chitosan beads in 0.5% and 0.1% Triton buffer, respectively.

Denaturation curves 516 corresponding to amplification curves 514 are provided as negative derivative plots of denaturation curves, −d(RFU)/dT, for a plurality of different DNA samples. Curve 522 is a denaturation curves for PC DNA amplified from a solution without using chitosan beads. Denaturation curve 524, corresponding to the amplification curve 520, is a denaturation curve for purified MCF7 DNA amplified directly from the chitosan beads surface according to the present invention. Curves 538 and 540 are denaturation for MCF7 DNA amplified from the surface of chitosan beads in 0.5% and 0.1% Triton solution, respectively.

Accordingly, FIGS. 4 and 5A-B (Examples 5 and 6) confirm that hgDNA can be amplified according to the method of the present invention Similarly, Examples 1 and 2 confirm that plasmids can be amplified according to the method of the present invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

All documents cited in this application ("herein-cited documents") and all documents cited or referenced in herein-cited documents are incorporated herein by reference in their entirety. In addition, any manufacturer's instructions or catalogues for any products cited or mentioned in each of the application documents or herein-cited documents are incorporated by reference in their entirety. Documents incorporated by reference into this text or any teachings therein can be used in the practice of this invention and, technology in each of the documents incorporated herein by reference can be used in the practice of this invention. Documents incorporated by reference into this text are not admitted to be prior art.

The invention claimed is:

1. A method of amplifying nucleic acids from a biological sample comprising the steps of:
adding microparticles to the biological sample, wherein the biological sample has a PCR amplification compatible pH, and wherein the microparticles are fabricated from chitosan;
mechanically agitating the biological sample to lyse cells in the biological sample;
capturing the released nucleic acids on the magnetic microparticles; and,
performing amplification directly on the captured nucleic acids, wherein the capturing of the nucleic acids on the magnetic microparticles is performed with the same buffer as the amplification.

2. The method of claim 1, wherein the lysis is performed by mechanically agitating the biological sample including vortexing the biological sample with the magnetic microparticles.

3. The method of claim 1, wherein the step of lysing the one or more cells in the biological sample includes heating the biological sample and vortexing the biological sample.

4. The method of claim 1, further comprising separating and washing microparticles with captured nucleic acids.

5. The method of claim 1, wherein interior of the chitosan microparticle, beneath a charge-switchable shell, remains positively charged at high pH.

6. The method of claim 1, wherein nucleic acids are selected from the group consisting of: plasmids, bacterial DNA, and human genomic DNA.

7. The method of claim 1, wherein the chitosan particles are fabricated by creating chitosan droplets in oil and then crosslinking the droplets into microparticles, wherein the crosslinking begins at the oil-water interface and continues into the core of the microparticle over time.

8. The method of claim 1, further comprising washing the microparticles twice with the oil solution, resuspending in the oil solution, and drying out with an air stream bubbling through the solution, wherein the oil solution is removed by washing the microparticles twice.

9. The method of claim 1, further comprising embedding magnetic nanoparticles within individual microparticles.

10. The method of claim 9, wherein the magnetic nanoparticles are iron nanoparticles measuring 20-40 nm in diameter.

* * * * *

SEQUENCE LISTING

```
<160> NUMBER OF SEQ ID NOS: 3

<210> SEQ ID NO 1
<211> LENGTH: 77
<212> TYPE: DNA
<213> ORGANISM: Artificial Sequence
<220> FEATURE:
<223> OTHER INFORMATION: PUC19 Plasmid DNA

<400> SEQUENCE: 1
agtgaattcg agctcggtac ccgggatcc tctagagtcg acctgcaggc atgcaagctt    60
ggcgtaatca tggtcat                                                  77
```

```
<210> SEQ ID NO 2
<211> LENGTH: 19
<212> TYPE: DNA
<213> ORGANISM: Artificial Sequence
<220> FEATURE:
<223> OTHER INFORMATION: Forward primer

<400> SEQUENCE: 2
gtctcatgag cggatacaa                                              19

<210> SEQ ID NO 3
<211> LENGTH: 20
<212> TYPE: DNA
<213> ORGANISM: Artificial Sequence
<220> FEATURE:
<223> OTHER INFORMATION: Reverse Primer

<400> SEQUENCE: 3
ctcgtgatac gcctattttt                                             20
```